US010480024B2

(12) United States Patent
Frayling et al.

(10) Patent No.: US 10,480,024 B2
(45) Date of Patent: Nov. 19, 2019

(54) SINGLE NUCLEOTIDE DETECTION METHOD

(71) Applicants: BASE4 INNOVATION LTD, Cambridge, Cambridgeshire (GB); MEDICAL RESEARCH COUNCIL, Swindon, Wiltshire (GB)

(72) Inventors: Cameron Alexander Frayling, Cambridgeshire (GB); Barnaby Balmforth, Cambridgeshire (GB); Bruno Flavio Nogueira de Sousa Soares, Cambridgeshire (GB); Thomas Henry Isaac, Cambridgeshire (GB); Boris Breiner, Cambridgeshire (GB); Alessandra Natale, Cambridgeshire (GB); Michele Amasio, Cambridgeshire (GB); Paul Dear, Wiltshire (GB)

(73) Assignees: BASE4 INNOVATION LTD, Cambridge, Cambridgeshire (GB); UNITED KINGDOM RESEARCH AND INNOVATION, Swindon (GB)

( * ) Notice: Subject to any disclaimer, the term of this patent is extended or adjusted under 35 U.S.C. 154(b) by 942 days.

(21) Appl. No.: 14/782,650

(22) PCT Filed: Apr. 9, 2014

(86) PCT No.: PCT/GB2014/051106
§ 371 (c)(1),
(2) Date: Oct. 6, 2015

(87) PCT Pub. No.: WO2014/167324
PCT Pub. Date: Oct. 16, 2014

(65) Prior Publication Data
US 2016/0040223 A1  Feb. 11, 2016

(30) Foreign Application Priority Data

Apr. 9, 2014 (GB) .................................. 1306445.6

(51) Int. Cl.
*C12Q 1/6869* (2018.01)
(52) U.S. Cl.
CPC .................................. *C12Q 1/6869* (2013.01)
(58) Field of Classification Search
None
See application file for complete search history.

(56) References Cited

U.S. PATENT DOCUMENTS

| 5,528,046 A | 6/1996 | Ishikawa |
| 5,674,743 A | 10/1997 | Ulmer |
| 6,268,146 B1 | 7/2001 | Shultz et al. |
| 2003/0138831 A1 | 7/2003 | Kwagh et al. |
| 2003/0187237 A1 | 10/2003 | Chan et al. |
| 2007/0015176 A1* | 1/2007 | Lao ....................... C12Q 1/6818 435/6.18 |
| 2007/0243634 A1* | 10/2007 | Pamula ............... B01F 13/0071 436/518 |
| 2007/0269817 A1 | 11/2007 | Shapero |
| 2009/0246788 A1 | 10/2009 | Albert et al. |
| 2009/0280475 A1 | 11/2009 | Pollack et al. |
| 2010/0184020 A1 | 7/2010 | Beer |
| 2012/0164633 A1 | 6/2012 | Laffler |

FOREIGN PATENT DOCUMENTS

| JP | 6-148076 | 5/1994 |
| WO | 94/18218 | 8/1994 |
| WO | 03/046216 | 6/2003 |
| WO | 03/080861 | 10/2003 |
| WO | 2004/002627 | 1/2004 |
| WO | 2006/115570 | 11/2006 |
| WO | 2010/077859 | 7/2010 |

OTHER PUBLICATIONS

Schweitzer et al. Proceedings of the National Academy of Sciences, USA 2000; 97: 10113-10119. (Year: 2000).*
Deutscher, M.P. and Kornberg, A. The Journal of Biological Chemistry 1969; 244: 3019-3028 (Year: 1969).*
Liu et al. BioTechniques 2000; 29: 1072-1083 (Year: 2000).*
Kunkel et al. The Journal of Biological Chemistry 1986; 261: 13610-13616 (Year: 1986).*
Written Opinion of Search Authority and International Search Report dated Jul. 24, 2014 in International (PCT) Application No. PCT/GB2014/051106.
Bayley, "Sequencing single molecules of DNA", Current Opinion in Chemical Biology, vol. 10, 2005, pp. 628-637.
Stephan et al., "Towards a general procedure for sequencing single DNA molecules", Journal of Biotechnology, vol. 86, 2001, pp. 255-267.
Search Report dated Oct. 7, 2013 in corresponding Great Britain Application No. 1306445.6.

* cited by examiner

*Primary Examiner* — Angela M. Bertagna
(74) *Attorney, Agent, or Firm* — Wenderoth, Lind & Ponack, L.L.P.

(57) ABSTRACT

A method for determining the sequence of nucleotide bases in a polynucleotide analyte is provided. It is characterised by the steps of (1) generating a stream of single nucleotide bases from the analyte; (2) producing captured molecules by reacting each single nucleotide base with a capture system; (3) amplifying at least part of the captured molecule to produce a plurality of amplicons characteristic of the single nucleotide base; (4) labelling the amplicons with a corresponding probe having a characteristic detectable element and (5) detecting a property characteristic of the detectable element.

50 Claims, 1 Drawing Sheet
Specification includes a Sequence Listing.

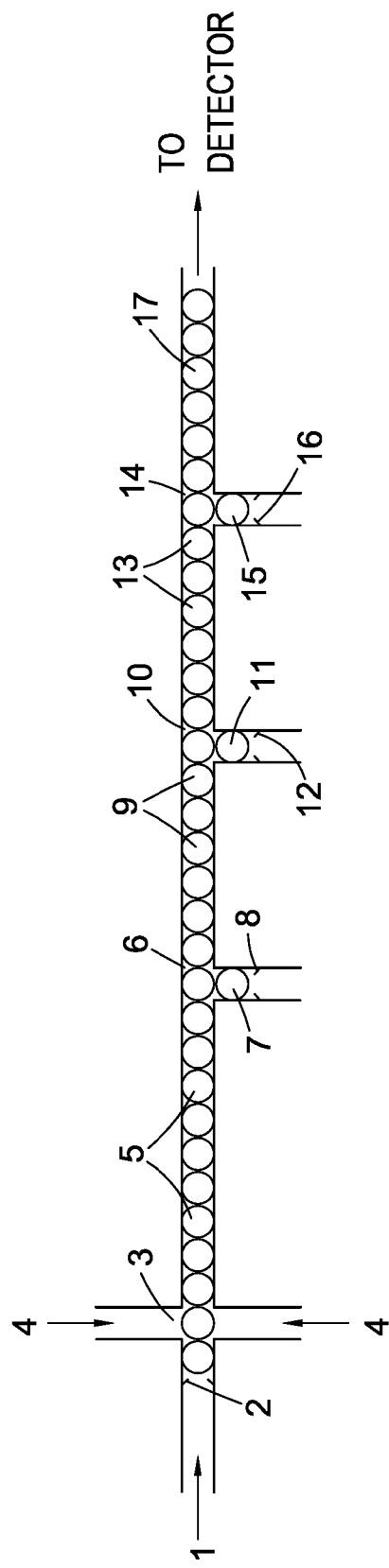

SINGLE NUCLEOTIDE DETECTION METHOD

This invention relates to a method for characterising RNA or DNA by detecting an ordered sequence of single nucleotide bases generated therefrom by progressive degradation.

Next generation sequencing of genetic material is already making a significant impact on the biological sciences in general and medicine in particular as the unit cost of sequencing falls in line with the coming to market of faster and faster sequencing machines. Thus, in one such machine, a double-stranded DNA analyte is first broken down into a plurality of smaller polynucleotide fragments each of which is first adenylated on both ends of one strand so that a single-stranded first oligonucleotide can be bound to both ends of its compliment by hybridisation to the unpaired adenine base. The treated fragments so obtained are then size-selected and captured on a surface coated with bound single-stranded second oligonucleotides which themselves are the sequence compliment of the first so that in effect a library of surface-bound double-stranded fragments can be created by further hybridisation. In a subsequent clustering step, these library components are then clonally amplified millions of times on the surface using extension and isothermal bridging reactions to utilise unused second oligonucleotides. This, in effect, creates a dense concentration of the polynucleotide fragment bound to the surface through one of its strands. The unbound complimentary strand of each fragment is then removed to leave bound single-stranded fragments ready for sequencing. In the sequencing stage, each of these single-stranded fragments is primed and its complimentary strand recreated by extension using the polymerase chain reaction and a mixture of the four characteristic nucleotide bases of DNA in dideoxynucleotide triphosphate (ddNTP) form. Each ddNTP type is end-blocked with a moiety which is labelled with a different fluorophore fluorescing at a different wavelength. The extension reaction then takes the form of a cycle of three steps; first the relevant ddNTP is bounded to the growing strand; secondly the nucleotide base it contains is identified by illuminating the sample and detecting the wavelength of the fluorescence and finally the end block and its associated fluorophore are removed to allow the next extension event to occur. By this means, the sequence of the complimentary strand can be built up base-by-base. It will be appreciated that, whilst this approach can be highly automated and can generate sequence reads of high accuracy, its speed of operation is limited by the rate of the extension cycle. Thus, in practice, use of the technology tends to involve parallel processing of relatively short polynucleotide fragments and assembly of the whole sequence from the various reads obtained therefrom. This in itself can lead to computational complexities and the potential introduction of errors.

More recently efforts have been made to develop direct sequencing methods. For example, WO 2009/030953 discloses a new fast sequencer in which inter alia the sequence of nucleotide bases or base pairs in a single- or double-stranded polynucleotide sample (e.g. naturally occurring RNA or DNA) is read by translocating the same through a nano-perforated substrate provided with plasmonic nano-structures juxtaposed within or adjacent the outlet of the nanopores. In this device, the plasmonic nanostructures define detection windows (essentially an electromagnetic field) within which each nucleotide base (optionally labelled) is in turn induced to fluoresce or Raman scatter photons in a characteristic way by interaction with incident light. The photons so generated are then detected remotely, multiplexed and converted into a data stream whose information content is characteristic of the nucleotide base sequence associated with the polynucleotide. This sequence can then be recovered from the data stream using computational algorithms embodied in corresponding software programmed into a microprocessor integral therewith or in an ancillary computing device attached thereto. Further background on the use of plasmonic nanostructures and their associated resonance characteristics can be found in for example Adv. Mat. 2004, 16(19) pp. 1685-1706.

Another apparatus for fast sequencing polynucleotides is described, for example, in U.S. Pat. Nos. 6,627,067, 6,267,872 and 6,746,594. In its simplest form, this device employs electrodes, instead of plasmonic nanostructures, to define the detection window across the substrate or in or around the outlet of the nanopore. A potential difference is then applied across the electrodes and changes in the electrical characteristics of the ionic medium flowing therebetween, as a consequence of the electrophoretic translocation of the polynucleotide and associated electrolyte through the nanopore, is measured as a function of time. In this device, as the various individual nucleotide bases pass through the detection window they continuously block and unblock it causing 'events' which give rise to characteristic fluctuations in current flow or resistivity. These fluctuations are then used to generate a suitable data stream for analysis as described above.

The generation of stable droplet streams, especially microdroplet streams, is another developing area of technology that already has applications in molecular biology. For example, U.S. Pat. No. 7,708,949 discloses a novel microfluidic method for generating stable water droplets in oil whilst for example US2011/0250597 describes utilisation of this technology to generate microdroplets containing a nucleic acid template (typically a polynucleotide DNA or RNA fragment) and a plurality of primer pairs that enable the template to be amplified using the polymerase chain reaction. Other patent applications relating to the field generally include JP2004/290977, JP2004/351417, US2012/0122714, US2011/0000560, US2010/01376163, US2010/0022414 and US2008/0003142.

WO 2004/002627 discloses a method for creating liquid-liquid and gas-liquid dispersions using various devices comprising creating a discontinuous section between upstream and downstream microfluidic regions. However its application to single nucleotide DNA sequencing is not taught.

WO 2010/077859 teaches a droplet actuator comprising a substrate provided with electrodes, a reactor path and nucleotide base, wash-buffer, sample and enzyme reservoirs. Whist the actuator is generically said to be useful for the amplification and sequencing of nucleic acids, there is no teaching of the analyte degradation method we describe below. Rather, it is concerned with a completely different approach; observing the synthesis of a complimentary strand of the analyte using pyrosequencing. US 2009/0280475 is concerned with similar subject-matter.

We have now developed a new sequencing method which in one embodiment involves generating a stream of nucleotide bases whose ordering is characteristic of the sequence in the analyte by progressive degradation of the analyte; and a subsequent capture of each nucleotide base in a way which enables it to be detected.

WO 94/18218 discloses a genome sequencer in which an ordered stream of single nucleotides is separated from an analyte and thereafter contained in a fluorescent-enhancing solid matrix where each nucleotide is excited using a laser and its characteristic spectroscopic emission detected. The single nucleotide transfer method used by this sequencer involves creating a single dual-sheath of flowing immiscible liquids rather than a series of droplets. Furthermore, the sequencer described seeks to detect the single nucleotides directly rather than employing a capture system and fluorophore release method of the type we describe. We believe that this is a drawback as it will lead to signal-to-noise ratio problems when the emissions come to be detected. This will compromise the overall sensitivity and therefore practical applicability of the sequencer itself.

Stephan et al Journal of Biotechnology 86 (2001) pp. 255-267 teaches a general method for counting single nucleotides generated by exonucleolytic degradation of an immobilised DNA sample labelled with fluorophores. However no information is provided about differentiating between the different single nucleotide types generated.

The use of the progressive pyrophosphorolytic degradation of polynucleotides to generate a stream of single nucleotide bases in the form of deoxyribonucleotide triphosphates has been disclosed in schematic form at mrc-lmb.cam.ac.uk/happy/HappyGroup/seq.html but little information about the actual methodology employed is provided. Furthermore, WO 03/080861 describes a sequencing method in which a DNA analyte is sequentially degraded to an ordered stream of single nucleotides by means of pyrophosphorolysis carried out in the presence of a pyrophosphate anion labelled with an intelligent dye. In one example the pyrophosphate anion is labelled with the dye JF-4 which has differing fluorescent lifetimes depending on the particular nucleotide type to which it is attached. The stream of labelled single nucleotides is then excited by a laser and analysed spectroscopically to determine the nature and therefore the ordering of the nucleotides. Once again the single nucleotides are detected directly rather than by employing the capture system and fluorophore release method we describe below. It is believed therefore that this method will also lead to signal-to-noise ratio and therefore sensitivity problems.

According to the present invention there is provided a method for determining the sequence of nucleotide bases in a polynucleotide analyte characterised by the steps of (1) generating a stream of single nucleotide bases from the analyte; (2) producing captured molecules by reacting each single nucleotide base with a capture system; (3) amplifying at least part of the captured molecule to produce a plurality of amplicons characteristic of the single nucleotide base; (4) labelling the amplicons with a corresponding probe having a characteristic detectable element and (5) detecting a property characteristic of the detectable element.

Step (1) of the method of the present invention comprises generating a stream of single nucleotide bases from a polynucleotide analyte. The analyte employed in this step is suitably a double-stranded polynucleotide comprised of many nucleotide bases. In principle, the length of the polynucleotide can be unlimited including up to the many millions of nucleotide bases found in a human genome fragment. The analyte itself is suitably RNA or DNA of natural origin although the method can also be used to sequence synthetically produced RNA or DNA or other nucleic acid made up wholly or in part of nucleotide bases that are not commonly encountered in nature; i.e. nucleotide bases other than adenine, thymine, guanine, cytosine and uracil. Examples of these include 4-acetylcytidine, 5-(carboxyhydroxylmethyl)uridine, 2-O-methylcytidine, 5-carboxymethylaminomethyl-2-thiouridine, 5-carboxymethylamino-methyluridine, dihydrouridine, 2-O-methylpseudouridine, 2-O-methylguanosine, inosine, N6-isopentyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, 5-methoxyuridine, 5-methoxycarbonylmethyl-2-thiouridine, 5-methoxycarbonylmethyluridine, 2-methylthio-N6-isopentenyladenosine, uridine-5-oxyacetic acid-methylester, uridine-5-oxyacetic acid, wybutoxosine, wybutosine, pseudouridine, queuosine, 2-thiocytidine, 5-methyl-2-thiouridine, 2-thiouridine, 4-thiouridine, 5-methyluridine, 2-O-methyl-5-methyluridine and 2-O-methyluridine.

Step (1) suitably further comprises a first sub-step of attaching the polynucleotide analyte to a substrate. Typically, the substrate comprises a microfluidic surface, a micro-bead or a permeable membrane made out of glass or a non-degradable polymer. Preferably, the substrate further comprises a surface adapted to receive the analyte. There are many ways in which the analyte can be attached to such surfaces all of which can in principle be used. For example, one method involves priming a glass surface with a functionalised silane such as an epoxysilane, an aminohydrocarbylsilane or a mercaptosilane. The reactive sites so generated can then be treated with a derivative of the analyte which has a terminal amine, succinyl or thiol group.

In one embodiment of step (1) the analyte is treated to generate a stream of single nucleotide bases the ordering of which corresponds to the former's sequence. This step is preferably carried out at a temperature in the range 20 to 90° C. in the presence of a reaction medium comprising an enzyme. Preferably this treatment is carried out under conditions of non-equilibrium flow so that the single nucleotide bases are continually removed from the reaction zone. Most preferably, the reaction is carried out by causing an aqueous buffered medium containing the enzyme to continuously flow over the surface to which the analyte is bound.

In a preferred form of this embodiment, the enzyme used in step (1) is one which can cause progressive 3'-5' pyrophosphorolytic degradation of the analyte to yield deoxyribonucleotide triphosphates at a reasonable reaction rate. Preferably this degradation rate is as fast as possible and in one embodiment lies in the range 1 to 50, preferably 1 to 20 nucleotide bases per second. Further information about the pyrophosphorolysis reaction as applied to polynucleotides can be found for example in J. Biol. Chem. 244 (1969) pp. 3019-3028. The enzyme which is employed in this pyrophosphorolysis reaction is suitably selected from the group consisting of those polymerases which show essentially neither exo- nor endonuclease activity under the reaction conditions. Examples of polymerases which can be advantageously used include, but are not limited to, the prokaryotic pol 1 enzymes or enzyme derivatives obtained from bacteria such as *Escherichia coli* (e.g. Klenow fragment polymerase), *Thermus aquaticus* (e.g. Taq Pol) and *Bacillus stearothermophilus, Bacillus caldovelox* and *Bacillus caldotenax*. Suitably, the pyrophosphorolytic degradation is carried out in the presence of a medium which further comprises pyrophosphate anion and magnesium cations in preferably millimolar concentrations. In another embodiment of the invention, deoxyribonucleotide triphosphates can be generated in two steps by treating the analyte with an exonuclease and a kinase.

In step (2) of the method of the present invention each single nucleotide base generated in step (1), is captured by a capture system itself comprising one or more oligomers of nucleotide bases. Preferably, before this step is carried out the aqueous medium containing the single nucleotide bases is treated with a pyrophosphatase to hydrolyse any residual pyrophosphate to phosphate anion.

In a first embodiment, the capture system comprises one of a class of pairs of first and second oligonucleotides. The first oligonucleotide in such a pair preferably comprises (a) a first double-stranded region and (b) a second single-stranded region comprised of n nucleotide bases wherein n is greater than 1 preferably greater than 5. In one sub-class, the first oligonucleotide can be regarded as having a molecular structure derived from a notional or actual single-stranded oligonucleotide precursor where the double-stranded region has been created by partially folding the 3' end of the precursor back on itself to generate a configuration which can be termed 'j shaped'. In another sub-class, the first oligonucleotide is generated by hybridising a third, shorter single-stranded oligonucleotide onto the 3' end of a longer fourth single-stranded oligonucleotide and then rendering the end of the resulting molecule which is double-stranded 'blunt' by means of a protecting group which for example bridges the end nucleotides of the two strands. Typically, the total length of the first oligonucleotide is up to 150 nucleotide bases, preferably between 20 and 100 nucleotide bases. At the same time it is preferred that the integer n is between 5 and 40, preferably between 10 and 30.

As regards the second oligonucleotide in the pair this is single-stranded and suitably has a nucleotide base sequence which is wholly or partially the compliment of that of the single-stranded region of the first oligonucleotide one nucleotide base beyond the end of the double-stranded region. The length of the second oligonucleotide is not critical and can be longer or shorter than the single stranded region to which it can bind although it is preferably not n−1 nucleotide bases long. More preferably, the length of the second oligonucleotide is chosen so that in the captured molecule a short overhang of unpaired nucleotide bases (e.g. 2 to 10 nucleotide bases) remains on one or other of the two strands thereof. Capture systems of this class work by attaching the single nucleotide base to the double-stranded end of the first oligonucleotide and hybridising and ligating the second oligonucleotide onto the remaining single-stranded region to generate a captured molecule which is double-stranded apart from its overhang.

In a second embodiment, the capture system comprises a class of single oligonucleotides each consisting of a single-stranded nucleotide region the ends of which are attached to two different double-stranded regions. In the capture systems of this class, the single-stranded nucleotide region is comprised of one nucleotide base only making the probe extremely selective for the detection of the target i.e. the complimentary single nucleotide base in the stream.

Turning to the double-stranded oligonucleotide region(s), it is preferred that they are derived or derivable from two oligonucleotide precursors, each preferably closed looped, or from a common single-stranded oligonucleotide precursor by folding the latters' ends back on themselves to create two closed-loop oligonucleotide base regions with an intermediate gap constituting the single-stranded nucleotide region. In all cases the effect is the same; adjacent to the ends of the single-stranded nucleotide region will be 3' and 5' free ends on the other strand of the oligonucleotide region to which the corresponding 5' and 3' ends of the target can be attached. Thus use of the capture system involves a process of attaching the single-stranded nucleotide region to the target single nucleotide base by joining it up with the available 3' and 5' ends of the capture system to generate a captured molecule which is double-stranded along its whole length.

Suitably, the double-stranded oligonucleotide region(s) are up to 50 nucleotide base pairs long, preferably up to 45 nucleotide base pairs, more preferably in the range 5 to 40 nucleotide base pairs and most preferably in the range 10 to 30. Longer regions may be used but the potential risk that access to the single-stranded nucleotide region by the target may become restricted through entanglement. This makes this embodiment potentially less attractive.

For both of the classes mentioned above, it is preferred in step (2) to employ simultaneously a mixture of at least two different sets of capture molecules each selective for a different complimentary nucleotide base and each having a characteristic nucleotide region to which a different characteristic probe can be bound by hybridisation. At least this characteristic nucleotide region is then amplified in step (3) to produce multiple amplicons to which the probe can be attached in step (4). When the analyte is DNA or RNA it is most preferred to employ four different capture systems at the same time with each one being selective for a different nucleotide base and a different probe.

Step (2) is suitably effected by contacting each single nucleotide base in the stream with the capture system, most preferably the four component capture system mentioned above, under conditions where the single nucleotide base is caused to be captured to generate the captured molecule which is either wholly double-stranded or double-stranded except for any degree of strand overhang mentioned above. This capturing is suitably effected by contacting the single nucleotide and the capture system together at a temperature in the range 30 to 80° C. in the presence of a two component enzyme system comprising a second polymerase and a ligase. In a preferred embodiment, the second polymerase is the same as that used in step (1) thereby avoiding the need to add this in the form of an extra component.

In step (3) of the method of the present invention, the captured molecule is amplified using any of the methods available in the art which are compatible with the product mixture generated in step (2). These methods include, but are not limited to, thermal cycling and isothermal methods such as the polymerase chain reaction, recombinase polymerase amplification and rolling circle amplification; the last of these being especially useful for captured molecules derived from the second class of capture molecule described above. By any of these means, many copies of a part of the captured molecule and its sequence compliment (typically referred to in the art as an amplicon) can be rapidly created. The exact methodologies for performing any of these amplification methods are well-known to one of ordinary skill and readily available in the literature. For example, in the case of the polymerase chain reaction, the methodology generally comprises (a) denaturing the captured molecule at elevated temperature so that it is in effect unzipped to a corresponding single-stranded state, (b) annealing a short single-stranded primer oligonucleotide onto the unzipped capture molecule at or near its 3' end, (c) extending the primer in the 5'-3' direction until the complimentary strand of the unzipped capture molecule is created; (d) denaturing the product of step (c) to regenerate the unzipped capture molecule and the complimentary strand both in single-stranded form and (e) repeating steps (b) to (d) multiple times to make multiple copies of the amplicons in an exponential fashion. Thus in practice step (3) comprises treating the product of step (2) with at least one primer, a polymerase and in the case of DNA for example a mixture of the four deoxyribonucleotide triphosphates characteristic thereof. Since step (3) involves the introduction of all four deoxyribonucleotide triphosphates it is important that capture of these added deoxyribonucleotide triphosphates by the capture system be prevented to avoid further captured molecules characteristic of the other nucleotide bases being generated. This may be achieved for example by inactivating the ligase employed in step (2) e.g. by heat treatment, before addition of the deoxyribonucleotide triphosphates. Otherwise, the reaction conditions and reagents used to carry out the polymerase chain reaction of step (3) are suitably those described in the art. In the case of the four-component system discussed above, step (3) will involve adding up to four different primer pairs each pair being selective for one or more of the four second oligonucleotides in the capture system. In a preferred embodiment, a single primer pair is used that is selective for all four second oligonucleotides in the capture system.

In step (4) of the method of the present invention, the amplicons are labelled with a probe having a characteristic detectable element. This step can be carried out once the final cycle of the amplification in step (3) is complete or more preferably at the same time as step (3) is occurring. Suitably the probe is one in which the detectable element is not detectable until the probe is bound to the amplicon and suitably the detectable property exhibited by the detectable element is fluorescence. Preferably the probe is an oligonucleotide which is able to bind to a unique sequence on its corresponding amplicon by hybridisation. In one embodiment, the probe employed is an example of those known in the art as molecular beacons. Molecular beacons are typically comprised of single-stranded oligonucleotides which have been in effect folded back onto themselves to create a residual single-stranded loop, which acts as the beacon's sensor, and a short stem where the nucleotide bases adjacent the two ends are bound to each other through complimentary nucleotide base pairing; thereby creating a double-stranded region. This arrangement, which can be likened to a hairpin in which the single-stranded loop is attached to complimentary strands of the same end of a notional double-stranded oligonucleotide, is highly strained. To the free 3' and 5' ends of the oligonucleotide (now adjacent to one another and at the remote end of the stem) are respectively attached a fluorophore and a quencher. Their geometric proximity to each other then ensures that in their unused state no significant fluorescence occurs. As used herein, the molecular beacon is chosen so that its loop can selectively hybridise to the unique sequence of the amplicon in doing so causing additional strain which unzips the stem of the beacon, causes distancing of the fluorophore and quencher and allows the beacon to fluoresce. Once again when employing the four component system described above, a mixture of four molecular beacons each selective for one of the amplicons is employed. Alternative probes which can be employed include, for example, Taqman probes, scorpion probes and molecules able to behave in a similar way.

Finally in step (5), the detectable elements activated by binding to the amplicons are detected enabling the particular single nucleotide base to be identified and the sequence of nucleotide bases in the analyte recovered from the data stream associated with the detection. Methods of doing this are well-known in the art; for example fluorescence from the activated molecular beacon may be detected using a photodetector or an equivalent device tuned to the characteristic fluorescence wavelength(s) or wavelength envelope(s) of its fluorophores. This in turn causes the photodetector to generate an electrical signal characteristic of the particular nucleotide base type which can be processed and thereafter analysed for example by a computer.

In a particularly preferred embodiment, the method of the present invention is carried out wholly or in part in microdroplets. Such a method may begin, for example, by inserting the single nucleotide bases generated in step (1) one-by-one into a corresponding stream of aqueous microdroplets in an immiscible carrier solvent such as a hydrocarbon or silicone oil to help preserve the ordering. Advantageously, this can be effected by directly creating the microdroplet downstream of the pyrophosphorolysis reaction zone for example by causing the reaction medium to emerge from a microdroplet head of suitable dimensions into a flowing stream of the solvent. Alternatively, small aliquots of the reaction medium can be sequentially injected into a stream of pre-existing aqueous microdroplets suspended in the solvent. If this latter approach is adopted, each microdroplet may suitably contain the components of the capture system and the various enzymes and any other reagents (e.g. buffer) required to effect step (2). Finally, the microdroplets created in the former embodiment can be caused to coalesce subsequently with a stream of such pre-exiting microdroplets to achieve a similar outcome. In this embodiment step (5) then preferably involves interrogating each droplet to identify the detectable elements which have been activated by the amplicons and hence the nature of the nucleotide base it contains.

To avoid the risk that a given microdroplet contains more than one single nucleotide base it is preferred to release the single nucleotide bases in step (1) at a rate such that each filled microdroplet is separated by from 1 to 20 preferably 2 to 10 empty ones. Thereafter the stream of filled and unfilled microdroplets in the solvent is caused to flow along a flow path, suitably a microfluidic flow path, at a rate and in a manner such that the microdroplets are maintained in a discrete state and do not have the opportunity to coalesce with each other. Suitably the microdroplets employed have a diameter less than 100 microns, preferably less than 50 microns, more preferably less than 20 microns and even more preferably less than 15 microns. Most preferably of all their diameters are in the range 2 to 20 microns. In one embodiment, the microdroplet flow rate through the whole system is in the range 50 to 3000 droplets per second preferably 100 to 2000.

The present invention will now be illustrated with reference to the following examples.

Preparation and Use of a Capture System

The following experiment illustrates the capture of a single nucleotide base and release of fluorophores using a capture system wherein the first oligonucleotide is j-shaped and the second is single-stranded.

A sample of a j-shaped oligonucleotide as described above is prepared by folding a 75 nucleotide base, single-stranded oligonucleotide having the following sequence: gtaggtcctggcacagaaaaaaggagGcagtgatgttccatgactgattttttttc agtcatggaacatcact*g (SEQ ID NO:1) wherein g, t, c, and a represent the conventional notation for the nucleotide bases of DNA and * represents the presence of a phosphorothioate linkage. Folding is carried out by heating an aqueous solution of this oligonucleotide to 95° C. and then cooling it slowly back to room temperature at a rate of 10 minutes per ° C. The j-shaped molecule so obtained comprises a residual single-stranded oligonucleotide region (gtaggtcctg-gcacagaaaaaaggag (SEQ ID NO:2)) attached to a single nucleotide base which is the site of capture (capitalised in the above-mentioned sequence).

A corresponding single-stranded oligonucleotide is also prepared, having the following sequence:
^ctccTTXTTtctgtgccaga (SEQ ID NO:3)
wherein ^ represents a 5' phosphate group, a capitalised T represents a thymine base labelled with Alexa Fluor 488 dye via an azide linker, and an X represents a thymine base labelled with a BHQ-1 quencher.

Separate capture and nucleotide base mixtures are then prepared. The capture mixture has a composition corresponding to that derived from the following formulation:
2.5 ul 10×BufferII
5 ul 10×Taq Ligase buffer (NEB)
2.5 ul 100 nM of the j-shaped molecules mentioned above
5 ul 100 nM of the single-stranded oligonucleotide mentioned above
2 ul Thermostable Inorganic Pyrophosphatase (NEB)
5 ul Taq Ligase (NEB)
1 ul 25 mM MnSO4
water to 25 ul
whilst the nucleotide base mixture, whose composition is designed to mimic the material, obtained from the pyrophosphorolysis step, corresponds to that derived from the formulation:
2.5 ul 10 BufferII (supplied with Amplitaq; magnesium-free)
1.5 ul MgCl2 25 mM
2.5 ul 10 nM of deoxycytidine triphosphate (dCTP)
2 ul Amplitaq (5U/ul)
2.5 ul 10 mM sodium pyrophosphate
water to 25 ul.

Capture of the dCTP is then effected by mixing together equal volumes of these two mixtures and incubating the resulting product at 50° C. This is typically complete in 30 minutes.

DROPLET MICROFLUIDIC METHOD USING THE CAPTURE SYSTEM

FIG. 1 schematically illustrates a microfluidic sequencing device in which microdroplets each containing a single nucleotide base are made to undergo reaction with a capture system of the type above as described above.

An aqueous medium 1 comprising a stream of single nucleotides obtained by the progressive pyrophosphorolysis of a 100 nucleotide base polynucleotide analyte derived from human DNA is caused to flow through a ten micron diameter microfluidic tube fabricated from PDMS polymer. The pyrophosphorolysis reaction itself is carried out at by passing a stream of an aqueous, buffered (pH 8) reaction medium at 72° C., comprising Taq Pol and a 2 millimoles per litre concentration of each of sodium pyrophosphate and magnesium chloride, over a glass micro bead onto which the analyte has been previously attached by means of a succinyl bridge. The order of the single nucleotide bases in 1, which is downstream of the micro bead, corresponds to the sequence of the analyte. 1 emerges from a droplet head 2 into a first chamber 3 where it is contacted with one or more streams of immiscible light silicone oil 4. The velocities of these streams are chosen to avoid turbulent mixing and to create aqueous spherical droplets 5 suspended in the oil each having a diameter of approximately eight microns. Typically, rates are adjusted so that between adjacent filled droplets there are 10 empty ones. A stream of 5 is then carried forward along a second microfluidic tube of the same diameter at a rate of 1000 droplets per second to a second chamber 6 into which a second stream of five micron aqueous spherical droplets 7 is also fed by means of a second droplet head 8. Droplets 5 and 7 are caused to coalesce in a sequential fashion to form enlarged aqueous droplets 9 approximately nine microns in diameter. Each of 7 contains pyrophosphatase to destroy any residual pyrophosphate anion present in each of 5.

A stream of 9 is then carried forward at the same rate via microfluidic tubing into a third chamber 10 where these droplets are contacted with a third stream of five micron aqueous spherical droplets 11 also fed thereto through a corresponding droplet head 12. The time taken for each of 9 to move between chambers 6 and 10 is c.2 minutes.

Droplets 9 and 11 are then caused to coalesce in 10 to produce droplets 13 approximately ten microns in diameter). Each of 11 contains a mesophilic ligase and a capture system comprising pairs of four j-shaped first oligonucleotides and four corresponding second single-stranded oligonucleotides. Each j-shaped first oligonucleotide is 60 nucleotide bases long and is prepared by folding a 60 nucleotide base single-stranded oligonucleotide precursor about the $45^{th}$ nucleotide base from the 5' end to generate 3 nucleotide single-stranded loop, a 12 nucleotide base pair double-stranded region and a 33 nucleotide base single-stranded region which is different in each of the four first oligonucleotides. Each of these four first oligonucleotides also has a different $33^{rd}$ base (measured from the single-stranded end) characteristic of the four characteristic nucleotide base types of DNA (i.e. A, T, G and C). The four different second oligonucleotides are each 28 nucleotide bases long and have different sequences which are complimentary to that part of the single-stranded region defined by the $4^{th}$ and $32^{nd}$ nucleotide bases of their first oligonucleotide pair.

A stream of 13 is next carried forward at the same rate via microfluidic tubing where after thirty minutes it is passed through a hot spot, where the ligase is caused to deactivate (ten to twenty minutes), before entering into a third chamber 14 where it is caused to coalesce with a fourth stream of five micron aqueous spherical droplets 15 also fed thereto through a droplet head 16. Each of 15 contains four different primer pairs selective for each of the second oligonucleotides, Taq Pol enzyme, the four deoxyribonucleotide triphosphates characteristic of DNA and four different molecular beacons selective for each of the four types of amplicons which can be generated from the four different captured molecules capable of being produced in 13. 15 may also contain other additives typically employed in carrying out the polymerase chain reaction. The stream of the coalesced microdroplets 17 so formed is then subjected to between 20 and 30 thermal cycles of between 60 and 95° C. (c. one cycle per minute) during which time amplification of the unzipped capture molecule occurs by the polymerase chain reaction. At the end of this time 17 is transferred to the detection system.

The detection system (not shown) typically comprises a detection window in which each droplet is interrogated with incident light from a laser. Action of this light then causes the activated molecular beacons in each droplet to fluoresce in a way characteristic of the single nucleotide base which was originally incorporated into the captured molecule (or essentially not at all if the droplet was originally empty). The presence or absence of this fluorescence is then detected at the four characteristic wavelengths of the four molecular beacons mentioned above. Thus as the droplets are interrogated in turn the sequence of nucleotide bases in the original polynucleotide analyte can in effect be read off. Although the onset of fluorescence is generally rapid, each droplet is interrogated only after ten minutes have elapsed to ensure that the empty droplets are reliably identified.

The invention claimed is:

1. A method for determining the sequence of nucleotide bases in a polynucleotide analyte, the method comprising steps of:
   (1) generating a stream of single nucleotide bases from the polynucleotide analyte, wherein the stream of single nucleotide bases is obtained by progressive pyrophosphorolysis of the polynucleotide analyte;
   (2) producing captured molecules by reacting each single nucleotide base with a capture system, wherein the capture system comprises different sets of capture molecules, each set being selective for a different nucleotide base;
   (3) for each captured molecule, amplifying at least part of the captured molecule to produce a plurality of amplicons;
   (4) for each captured molecule, labelling the amplicons with a corresponding probe selective for the amplicons and comprising a different detectable element, wherein the probes are present in a mixture of probes each selective for a different nucleotide base;
   (5) for each captured molecule, detecting a property characteristic of the detectable element; and
   (6) from the totality of the results of step (5), determining the sequence of nucleotide bases in the polynucleotide analyte.

2. The method as claimed in claim 1, wherein the capture system is comprised of two components for each different nucleotide base: (a) a first oligonucleotide comprising a double-stranded region and a single-stranded region and (b) a second oligonucleotide that is single-stranded and whose nucleotide base sequence is at least partially complementary to that of the single-stranded region of the first oligonucleotide one nucleotide base beyond the end of the double-stranded region.

3. The method as claimed in claim 2, wherein the first oligonucleotide is j-shaped.

4. The method as claimed in claim 2, wherein the total length of the first oligonucleotide is from 20 to 100 nucleotide bases.

5. The method as claimed in claim 1, wherein the capture system comprises a single oligonucleotide for each different nucleotide base, consisting of a single-stranded nucleotide region the ends of which are attached to two different double-stranded oligonucleotide regions.

6. The method as claimed in claim 5, wherein each double-stranded oligonucleotide region is comprised of from 10 to 30 nucleotide pairs.

7. The method as claimed in claim 5, wherein two discrete double-stranded oligonucleotide regions are employed, each comprising ends remote from the single-stranded nucleotide region which are closed-looped.

8. The method as claimed in claim 5, wherein the double-stranded oligonucleotide regions are derivable from a single-stranded oligonucleotide precursor by folding the ends back on themselves to leave a gap comprising the single-stranded nucleotide region.

9. The method as claimed in claim 1, wherein the polynucleotide analyte is bound to a surface.

10. The method as claimed in claim 1, wherein step (1) is carried out under non-equilibrium conditions in the presence of a flowing aqueous medium comprising an enzyme, a pyrophosphate anion and magnesium cations, and wherein the single nucleotide bases are continuously removed from a reaction zone where they are generated.

11. The method as claimed in claim 10, wherein between steps (1) and (2), any residual pyrophosphate anion is destroyed by means of a pyrophosphatase.

12. The method as claimed in claim 1, wherein the capture system comprises four different first oligonucleotides, each of which has one of four different single-stranded regions, and four different second oligonucleotides, each of which has a sequence complementary to a part of one of the four different single-stranded regions in the four different first oligonucleotides.

13. The method as claimed in claim 1, wherein steps (3) and (4) are carried out simultaneously.

14. The method as claimed in claim 1, wherein the amplification in step (3) is carried out using a method selected from the polymerase chain reaction, recombinase polymerase amplification and rolling circle amplification.

15. The method as claimed in claim 1, wherein step (2) employs a ligase which is deactivated before step (4) occurs.

16. The method as claimed in claim 1, wherein the probes are molecular beacons.

17. The method as claimed in claim 1, wherein in step (5) the detectable element is a fluorophore and fluorescence emitted by fluorophores is detected.

18. The method as claimed in claim 1, wherein at least one of steps (1) to (5) is carried out in microdroplets.

19. A method for determining the sequence of nucleotide bases in a polynucleotide analyte, the method comprising steps of:
  (1) generating a stream of single nucleotide bases from the polynucleotide analyte;
  (2) producing captured molecules by reacting each single nucleotide base with a capture system, wherein the capture system comprises different sets of capture molecules, each set being selective for a different nucleotide base, and wherein the capture system is comprised of two components for each different nucleotide base: (a) a first oligonucleotide comprising a double-stranded region and a single-stranded region and (b) a second oligonucleotide that is single-stranded and whose nucleotide base sequence is at least partially complementary to that of the single-stranded region of the first oligonucleotide one nucleotide base beyond the end of the double-stranded region;
  (3) for each captured molecule, amplifying at least part of the captured molecule to produce a plurality of amplicons;
  (4) for each captured molecule, labelling the amplicons with a corresponding probe that is selective for the amplicons and comprising a different detectable element, wherein the probes are present in a mixture of probes each selective for a different nucleotide base;
  (5) for each captured molecule, detecting a property characteristic of the detectable element; and
  (6) from the totality of the results of step (5), determining the sequence of nucleotide bases in the polynucleotide analyte.

20. The method as claimed in claim 19, wherein the stream of single nucleotide bases in step (1) is obtained by action of (i) a kinase and (ii) an exonuclease.

21. The method as claimed in claim 19, wherein the polynucleotide analyte is bound to a surface.

22. The method as claimed in claim 19, wherein step (1) is carried out under non-equilibrium conditions in the presence of a flowing aqueous medium comprising an enzyme, a pyrophosphate anion and magnesium cations, and wherein the single nucleotide bases are continuously removed from a reaction zone where they are generated.

23. The method as claimed in claim 22, wherein between steps (1) and (2), any residual pyrophosphate anion is destroyed by means of a pyrophosphatase.

24. The method as claimed in claim 19, wherein the first oligonucleotide is j-shaped.

25. The method as claimed in claim 19, wherein the total length of the first oligonucleotide is from 20 to 100 nucleotide bases.

26. The method as claimed in claim 19, wherein the polynucleotide analyte is DNA or RNA, and the capture system comprises four different sets of capture molecules, each set being selective for a different nucleotide base of the DNA or RNA.

27. The method as claimed in claim 19, wherein steps (3) and (4) are carried out simultaneously.

28. The method as claimed in claim 19, wherein the amplification in step (3) is carried out using a method selected from the polymerase chain reaction, recombinase polymerase amplification and rolling circle amplification.

29. The method as claimed in claim 19, wherein step (2) employs a ligase which is deactivated before step (4) occurs.

30. The method as claimed in claim 19, wherein the probes are molecular beacons.

31. The method as claimed in claim 19, wherein in step (5) the detectable element is a fluorophore and fluorescence emitted by fluorophores is detected.

32. The method as claimed in claim 19, wherein at least one of steps (1) to (5) is carried out in microdroplets.

33. A method for determining the sequence of nucleotide bases in a polynucleotide analyte, the method comprising steps of:
  (1) generating a stream of single nucleotide bases from the polynucleotide analyte, wherein step (1) is carried out in the presence of a reaction medium comprising a polymerase that exhibits neither exonuclease or endonuclease behaviour under conditions of a pyrophosphorolysis reaction;

(2) producing captured molecules by reacting each single nucleotide base with a capture system, wherein the capture system comprises different sets of capture molecules, each set being selective for a different nucleotide base;

(3) for each captured molecule, amplifying at least part of the captured molecule to produce a plurality of amplicons;

(4) for each captured molecule, labelling the amplicons with a corresponding probe that is selective for the amplicons and comprising a different detectable element, wherein the probes are present in a mixture of probes each selective for a different nucleotide base;

(5) for each captured molecule, detecting a property characteristic of the detectable element; and (6) from the totality of the results of step (5), determining the sequence of nucleotide bases in the polynucleotide analyte.

34. The method as claimed in claim 33, wherein the capture system is comprised of two components for each different nucleotide base: (a) a first oligonucleotide comprising a double-stranded region and a single-stranded region and (b) a second oligonucleotide that is single-stranded and whose nucleotide base sequence is at least partially complementary to that of the single-stranded region of the first oligonucleotide one nucleotide base beyond the end of the double-stranded region.

35. The method as claimed in claim 34, wherein the first oligonucleotide is j-shaped.

36. The method as claimed in claim 34, wherein the total length of the first oligonucleotide is from 20 to 100 nucleotide bases.

37. The method as claimed in claim 33, wherein the capture system comprises a single oligonucleotide for each different nucleotide base, consisting of a single-stranded nucleotide region the ends of which are attached to two different double-stranded oligonucleotide regions.

38. The method as claimed in claim 37, wherein each double-stranded oligonucleotide region is comprised of from 10 to 30 nucleotide pairs.

39. The method as claimed in claim 37, wherein two discrete double-stranded oligonucleotide regions are employed, each comprising ends remote from the single-stranded nucleotide region which are closed-looped.

40. The method as claimed in claim 37, wherein the double-stranded oligonucleotide regions are derivable from a single-stranded oligonucleotide precursor by folding the ends back on themselves to leave a gap comprising the single-stranded nucleotide region.

41. The method as claimed in claim 33, wherein the polynucleotide analyte is bound to a surface.

42. The method as claimed in claim 33, wherein step (1) is carried out under non-equilibrium conditions in the presence of a flowing aqueous medium comprising the polymerase, a pyrophosphate anion and magnesium cations, and wherein the single nucleotide bases are continuously removed from a reaction zone where they are generated.

43. The method as claimed in claim 42, wherein between steps (1) and (2), any residual pyrophosphate anion is destroyed by means of a pyrophosphatase.

44. The method as claimed in claim 33, wherein the polynucleotide analyte is DNA or RNA, and the capture system comprises four different sets of capture molecules, each set being selective for a different nucleotide base of the DNA or RNA.

45. The method as claimed in claim 33, wherein steps (3) and (4) are carried out simultaneously.

46. The method as claimed in claim 33, wherein the amplification in step (3) is carried out using a method selected from the polymerase chain reaction, recombinase polymerase amplification and rolling circle amplification.

47. The method as claimed in claim 33, wherein step (2) employs a ligase which is deactivated before step (4) occurs.

48. The method as claimed in claim 33, wherein the probes are molecular beacons.

49. The method as claimed in claim 33, wherein in step (5) the detectable element is a fluorophore and fluorescence emitted by fluorophores is detected.

50. The method as claimed in claim 33, wherein at least one of steps (1) to (5) is carried out in microdroplets.

* * * * *

SEQUENCE LISTING

```
<160> NUMBER OF SEQ ID NOS: 3

<210> SEQ ID NO 1
<211> LENGTH: 75
<212> TYPE: DNA
<213> ORGANISM: Artificial Sequence
<220> FEATURE:
<223> OTHER INFORMATION: j-shaped oligonucleotide precursor
<220> FEATURE:
<221> NAME/KEY: misc_feature
<222> LOCATION: (74)..(75)
<223> OTHER INFORMATION: Phosphorothioate linkage

<400> SEQUENCE: 1
gtaggtcctg gcacagaaaa aaggaggcag tgatgttcca tgactgattt tttttttcagt    60 catggaacat cactg                                                     75

<210> SEQ ID NO 2
<211> LENGTH: 26
<212> TYPE: DNA
<213> ORGANISM: Artificial Sequence
<220> FEATURE:
<223> OTHER INFORMATION: Residual single-stranded oligonucleotide region
      of j-shaped oligonucleotide

<400> SEQUENCE: 2
gtaggtcctg gcacagaaaa aaggag                                         26

<210> SEQ ID NO 3
<211> LENGTH: 20
<212> TYPE: DNA
<213> ORGANISM: Artificial Sequence
<220> FEATURE:
<223> OTHER INFORMATION: single-stranded oligonucleotide
<220> FEATURE:
<221> NAME/KEY: misc_feature
<222> LOCATION: (5)..(6)
<223> OTHER INFORMATION: Thymine bases labelled with Alexa Fluor 488 via
      azide linker
<220> FEATURE:
<221> NAME/KEY: misc_feature
<222> LOCATION: (7)..(7)
<223> OTHER INFORMATION: Thymine base labelled with BHQ-1 quencher
<220> FEATURE:
<221> NAME/KEY: misc_feature
<222> LOCATION: (8)..(9)
<223> OTHER INFORMATION: Thymine bases labelled with Alexa Fluor 488 via
      azide linker

<400> SEQUENCE: 3
ctcctttttt ctgtgccaga                                                20
```